US010740642B2

(12) United States Patent
Sakuragi

(10) Patent No.: US 10,740,642 B2
(45) Date of Patent: Aug. 11, 2020

(54) IMAGE DISPLAY CONTROL DEVICE, METHOD, AND PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 59 days.

(21) Appl. No.: 16/155,350

(22) Filed: Oct. 9, 2018

(65) Prior Publication Data

US 2019/0050665 A1 Feb. 14, 2019

Related U.S. Application Data

(63) Continuation of application No. PCT/JP2017/009673, filed on Mar. 10, 2017.

(30) Foreign Application Priority Data

Apr. 11, 2016 (JP) .................................. 2016-078634

(51) Int. Cl.
*G06T 19/00* (2011.01)
*G06T 7/33* (2017.01)
(Continued)

(52) U.S. Cl.
CPC ............ *G06K 9/3241* (2013.01); *A61B 6/022* (2013.01); *A61B 6/4417* (2013.01); *A61B 6/463* (2013.01);
(Continued)

(58) Field of Classification Search
CPC .......... G06K 9/3241; G02B 2027/0127; G02B 2027/0118; G02B 2027/0178;
(Continued)

(56) References Cited

U.S. PATENT DOCUMENTS

| 5,335,173 | A | * | 8/1994 | Sasahara | ................ | G16H 50/50 600/407 |
| 8,970,693 | B1 | * | 3/2015 | Chang | ................... | G06T 19/006 348/136 |

(Continued)

FOREIGN PATENT DOCUMENTS

| JP | H01-037678 A | 2/1989 |
| JP | S64-037678 A | 2/1989 |

(Continued)

OTHER PUBLICATIONS

An Office Action mailed by the Japanese Patent Office dated Oct. 1, 2019, which corresponds to Japanese Patent Application No. 2018-511934 and is related to U.S. Appl. No. 16/155,350; with English translation.

(Continued)

*Primary Examiner* — Tapas Mazumder
(74) *Attorney, Agent, or Firm* — Studebaker & Brackett PC

(57) ABSTRACT

The image display control device includes an image extracting unit that extracts an image of an observing target tissue from a three-dimensional image, a distance storage unit that stores a distance from a front surface of the observing target tissue to be used for generating a superimposition image, a surface form obtaining unit that obtains a surface form of the observing target tissue in a real space, a position matching unit that performs position matching such that a positional matching relationship between the surface form in the real space and the image of the observing target tissue is established, a superimposition image generating unit that generates the superimposition image based on the image of the observing target tissue on which the position matching is performed and the distances, and a display controller that displays the superimposition image such that the superim- (Continued)

position image is superimposed on the observing target tissue.

17 Claims, 5 Drawing Sheets

(51) Int. Cl.
| | | |
|---|---|---|
| G06K 9/32 | (2006.01) | |
| G02B 27/01 | (2006.01) | |
| A61B 6/00 | (2006.01) | |
| A61B 90/00 | (2016.01) | |
| G02B 30/00 | (2020.01) | |
| A61B 6/02 | (2006.01) | |
| A61B 6/03 | (2006.01) | |
| A61B 90/50 | (2016.01) | |

(52) U.S. Cl.
CPC ............ *A61B 6/466* (2013.01); *A61B 6/5247* (2013.01); *A61B 90/37* (2016.02); *G02B 27/017* (2013.01); *G02B 27/0172* (2013.01); *G02B 30/00* (2020.01); *G06T 7/337* (2017.01); *G06T 19/006* (2013.01); *A61B 6/032* (2013.01); *A61B 6/037* (2013.01); *A61B 2090/365* (2016.02); *A61B 2090/371* (2016.02); *A61B 2090/372* (2016.02); *A61B 2090/374* (2016.02); *A61B 2090/3762* (2016.02); *A61B 2090/502* (2016.02); *G02B 2027/014* (2013.01); *G02B 2027/0118* (2013.01); *G02B 2027/0127* (2013.01); *G02B 2027/0134* (2013.01); *G02B 2027/0178* (2013.01); *G06T 2207/10081* (2013.01); *G06T 2207/30056* (2013.01); *G06T 2210/41* (2013.01)

(58) Field of Classification Search
CPC .. G02B 30/00; G02B 27/017; G02B 27/0172; G02B 2027/0134; G02B 2027/014; G06T 2210/41; G06T 2207/30056; G06T 2207/10081; G06T 19/006; G06T 7/337; A61B 6/4417; A61B 6/5247; A61B 6/463; A61B 90/37; A61B 6/022; A61B 6/466; A61B 2090/3762; A61B 6/032; A61B 2090/374; A61B 2090/502; A61B 6/037; A61B 2090/365; A61B 2090/371; A61B 2090/372
See application file for complete search history.

(56) References Cited

U.S. PATENT DOCUMENTS

| | | | |
|---|---|---|---|
| 2007/0238981 A1 | 10/2007 | Zhu et al. | |
| 2010/0177163 A1 | 7/2010 | Yang et al. | |
| 2014/0193789 A1 | 7/2014 | Imanaka et al. | |
| 2014/0333617 A1* | 11/2014 | Miyamoto | ............ A61B 34/10 345/420 |
| 2015/0133764 A1* | 5/2015 | Sakuragi | ................ A61B 34/10 600/407 |
| 2016/0187969 A1* | 6/2016 | Larsen | .................... G06F 3/012 345/156 |

FOREIGN PATENT DOCUMENTS

| | | |
|---|---|---|
| JP | 2003199707 A | 7/2003 |
| JP | 2009-529951 A | 8/2009 |
| JP | 2010-532035 A | 9/2010 |
| JP | 2010-259497 A | 11/2010 |
| JP | 2011-212367 A | 10/2011 |
| JP | 2012-235983 A | 12/2012 |
| JP | 2013-045284 A | 3/2013 |
| WO | 2013/014868 A1 | 1/2013 |

OTHER PUBLICATIONS

International Search Report issued in PCT/JP2017/009673; dated May 23, 2017.
International Preliminary Report on Patentability and Written Opinion issued in PCT/JP2017/009673; dated Oct. 16, 2018.

* cited by examiner

IMAGE DISPLAY CONTROL DEVICE, METHOD, AND PROGRAM

CROSS-REFERENCE TO RELATED APPLICATIONS

This application is a Continuation of PCT International Application No. PCT/JP2017/009673 filed on Mar. 10, 2017, which claims priority under 35 U.S.C § 119(a) to Patent Application No. 2016-078634 filed in Japan on Apr. 11, 2016, all of which are hereby expressly incorporated by reference into the present application.

BACKGROUND OF THE INVENTION

1. Field of the Invention

The present invention relates to image display control device, method, and non-transitory computer readable recording medium storing program which display a superimposition image in a real space by using augmented reality.

2. Description of the Related Art

In the related art, a virtual object created from a medical image captured before surgery is displayed so as to be superimposed in a real space by a head-mounted display, and thus, surgery simulation and surgery navigation are used (for example, see JP2011-212367A).

JP2010-259497A and JP2012-235983A suggest that surgery is safely performed by obtaining a surface form of an organ in a real space by using a camera and a sensor, performing position matching (registration) on an organ model generated from an image obtained by a computed tomography (CT) device before the surgery, and displaying the organ model such that the organ model is superimposed on the surface form.

SUMMARY OF THE INVENTION

However, as in JP2010-259497A and JP2012-235983A, since there is no depth perception in the organ model itself by merely displaying the organ model such that the organ model is superimposed on surface form, in a case where the surgery is performed while referring to the organ model displayed so as to be superimposed in resection surgery of a liver, blood vessels present on a deeper side from an actual organ are displayed so as to be superimposed, and it is difficult to ascertain how the blood vessel present directly below a front surface of the organ runs.

The present invention has been made in view of the aforementioned circumstances, and an object of the present invention is to provide image display control device, method, and non-transitory computer readable recording medium storing a program capable of displaying a superimposition image with which it is easy to ascertain depth information such that the superimposition image is superimposed on an observing target tissue in a real space.

An image display control device according to the present invention comprises an image extracting unit that extracts an image of an observing target tissue from a three-dimensional image obtained by imaging a testing subject, a distance storage unit that stores a distance from a front surface of the observing target tissue to be used for generating a superimposition image to be displayed so as to be superimposed on the observing target tissue, a surface form obtaining unit that obtains a surface form of the observing target tissue in a real space, a position matching unit that performs position matching such that a positional matching relationship between the surface form in the real space and the image of the observing target tissue is established, a superimposition image generating unit that generates the superimposition image based on the image of the observing target tissue on which the position matching is performed and the distance stored in the distance storage unit, and a display controller that displays the superimposition image such that the superimposition image is superimposed on the observing target tissue.

In the image display control device according to the present invention, the surface form obtaining unit may obtain the surface form measured by a surface form measuring unit that measures the surface form of the observing target tissue in the real space, and the surface form measuring unit may measure the surface form by measuring a distance between the surface form measuring unit and each of a plurality of points on the front surface of the observing target tissue in the real space.

In the image display control device according to the present invention, the surface form obtaining unit may sequentially obtain the surface form in the real space with elapse of time, the position matching unit may sequentially perform the position matching according to the obtaining of the surface form, and the superimposition image generating unit may sequentially update the superimposition image according to the position matching.

The image display control device according to the present invention may further comprise a distance change accepting unit that accepts a change of the distance. The superimposition image generating unit generates the superimposition image based on the changed distance and the image of the observing target tissue.

In the image display control device according to the present invention, the superimposition image generating unit may generate the superimposition image by setting a transparency higher than a transparency of the image of the observing target tissue within the distance for the image of the observing target tissue in a range out of the distance.

In the image display control device according to the present invention, the transparency set for the image of the observing target tissue in the range out of the distance may be set so as to gradually become higher as the image is farther away from the distance.

In the image display control device according to the present invention, the superimposition image generating unit may generate the superimposition image by setting the same opacity as an opacity of the image of the observing target tissue within the distance for an image of a preset specific tissue in the range out of the distance.

In the image display control device according to the present invention, in a case where the image of the specific tissue is displayed, the display controller may display, as text, a distance of the specific tissue from the front surface of the observing target tissue.

The image display control device according to the present invention may further comprise an imaging unit that images the image of the observing target tissue in the real space. The display controller may display the superimposition image such that the superimposition image is superimposed on the image of the observing target tissue captured by the imaging unit.

In the image display control device according to the present invention, the display controller may display the superimposition image on a see-through type monitor.

An image display control method according to the present invention comprises extracting an image of an observing target tissue from a three-dimensional image obtained by imaging a testing subject, storing a distance from a front surface of the observing target tissue to be used for generating a superimposition image to be displayed so as to be superimposed on the observing target tissue in advance, obtaining a surface form of the observing target tissue in a real space, performing position matching such that a positional matching relationship between the surface form in the real space and the image of the observing target tissue is established, generating the superimposition image based on the image of the observing target tissue on which the position matching is performed and the distance stored in advance, and displaying the superimposition image such that the superimposition image is superimposed on the observing target tissue.

A non-transitory computer readable recording medium storing an image display control program according to the present invention causes a computer to perform a procedure of extracting an image of an observing target tissue from a three-dimensional image obtained by imaging a testing subject, a procedure of storing a distance from a front surface of the observing target tissue to be used for generating a superimposition image to be displayed so as to be superimposed on the observing target tissue in advance, a procedure of obtaining a surface form of the observing target tissue in a real space, a procedure of performing position matching such that a positional matching relationship between the surface form in the real space and the image of the observing target tissue is established, a procedure of generating the superimposition image based on the image of the observing target tissue on which the position matching is performed and the distance stored in advance, and a procedure of displaying the superimposition image such that the superimposition image is superimposed on the observing target tissue.

In accordance with the image display control device, method, and non-transitory computer readable recording medium storing a program according to the present invention, the image of the observing target tissue is extracted from the three-dimensional image obtained by imaging the testing subject, obtains the surface form of the observing target tissue in the real space, and the position matching is performed such that the positional matching relationship between the surface form in the real space and the image of the observing target tissue is established. The superimposition image is generated based on the image of the observing target tissue on which the position matching is performed and the distance stored in advance, and the superimposition image is displayed so as to be superimposed on the observing target tissue. The superimposition image with which it is easy to ascertain the depth information can be displayed so as to be superimposed on the observing target tissue in the real space by generating the superimposition image corresponding to the distance stored in advance in this manner and displaying the superimposition image such that the superimposition image is superimposed on the observing target tissue.

DESCRIPTION OF THE PREFERRED EMBODIMENTS

Figure 1:
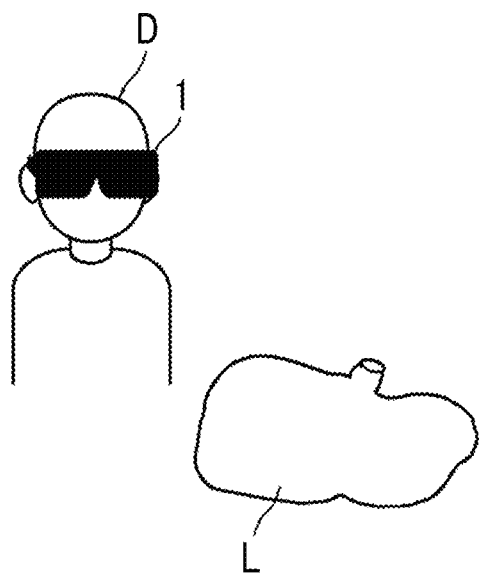
FIG. 1 is a diagram for describing a use situation of a virtual object display system using an embodiment of an image display control device according to the present invention.

Hereinafter, an embodiment of a virtual object display system using an embodiment of an image display control device according to an embodiment of the present invention will be described with reference to the drawings. FIG. 1 is a diagram for describing a use situation of the virtual object display system according to the present embodiment.

The virtual object display system according to the present embodiment displays a three-dimensional image of a liver L (observing target tissue), as a virtual object, by using augmented reality in a case where surgery is performed for the liver L, for example. Specifically, the three-dimensional image of the observing target tissue such as the liver L, is extracted from a three-dimensional image obtained by imaging the abdomen of a patient (testing subject) to undergo surgery, and the virtual object is generated by using the three-dimensional image thereof. For example, the virtual object is displayed on a head-mounted display (hereinafter, referred to as an HMD) 1 worn by a surgeon D who performs surgery. The virtual object is displayed so as to be superimposed on the liver L, and the surgeon D may perform the surgery of the liver L while observing the virtual object. The virtual object displayed on the HMD 1 corresponds to a superimposition image according to the embodiment of the present invention. Hereinafter, the virtual object is referred to as the superimposition image.

Figure 2:
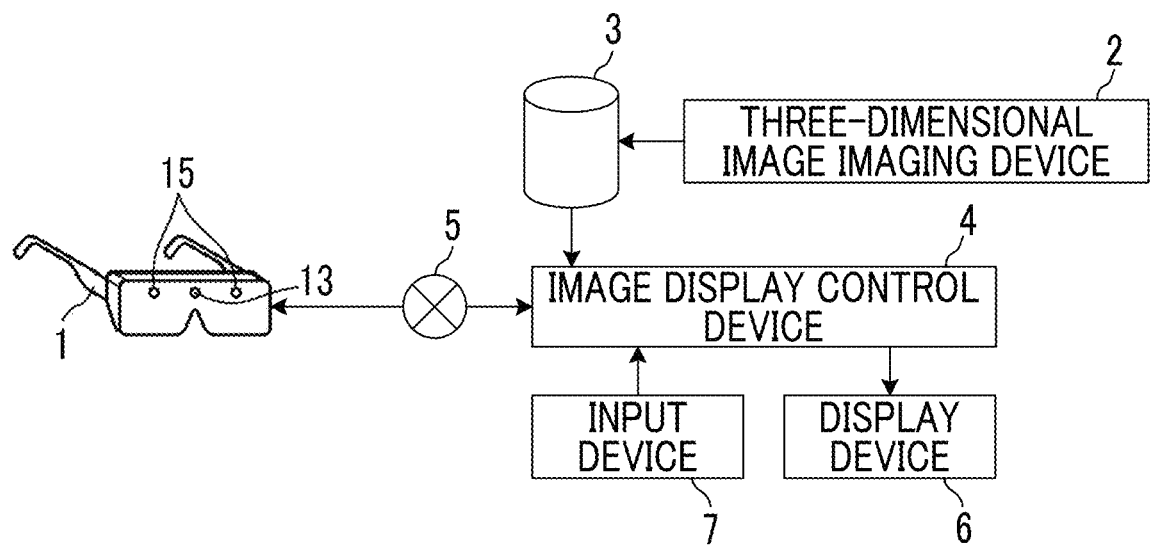
FIG. 2 is a hardware configuration diagram showing an outline of the virtual object display system shown in FIG. 1.

FIG. 2 is a hardware configuration diagram showing an outline of the virtual object display system according to the present embodiment. As shown in FIG. 2, the virtual object display system according to the present embodiment comprises the HMD 1, a three-dimensional image imaging device 2, an image storage server 3, and an image display control device 4. The HMD 1 and the image display control device 4 are connected so as to wirelessly communicate with each other via a network 5. The image storage server 3, a display device 6, and an input device 7 are connected to the image display control device 4.

The three-dimensional image imaging device 2 is a device that generates a three-dimensional image V0 representing a part as a surgery target of the patient by imaging the part, and is specifically a CT device, a magnetic resonance imaging (MM) device, or a positron emission tomography (PET) device. The three-dimensional image V0 generated by the three-dimensional image imaging device 2 is transmitted to and is stored in the image storage server 3. In the present embodiment, it is assumed that the abdomen is captured by the CT device by using the CT device as the three-dimensional image imaging device 2 and the three-dimensional image V0 of the abdomen is generated.

The image storage server 3 is a computer that stores and manages various data items, and comprises a large-capacity external storage device and database management software. The image storage server 3 obtains image data such as the three-dimensional image V0 generated by the three-dimensional image imaging device 2 via the network, and stores and manages the obtained image data in a recording medium such as the large-capacity external storage device.

Figure 3:
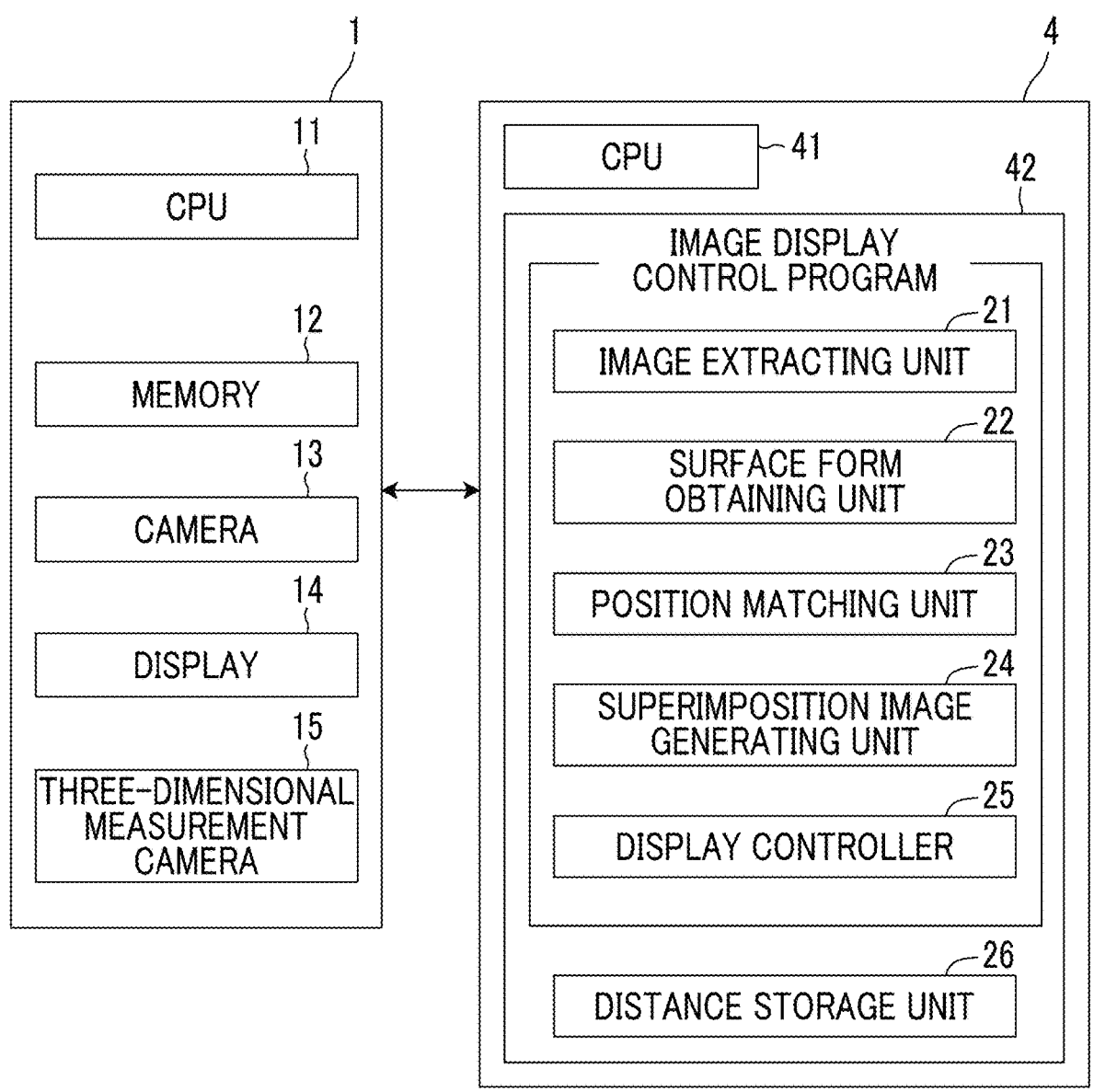
FIG. 3 is a block diagram showing a schematic configuration of a head-mounted display and an image display control device.

FIG. 3 is a block diagram showing schematic configurations of the HMD 1 and the image display control device 4. As shown in FIG. 3, the HMD 1 comprises a central processing unit (CPU) 11, a memory 12, a camera 13, a display 14, and a three-dimensional measurement camera 15. In the present embodiment, the camera 13 corresponds to an imaging unit according to the embodiment of the present invention, and the three-dimensional measurement camera 15 corresponds to a surface form measuring unit according to the embodiment of the present invention.

The CPU 11 controls the entire HMD 1. Particularly, the CPU 11 displays the superimposition image on the display 14 based on a control signal output from the display controller 25 of the image display control device 4.

The memory 12 stores an image captured by the camera 13 and the three-dimensional measurement camera 15.

The camera 13 comprises a lens and an imaging element such as a charge coupled device (CCD). As shown in FIG. 2, the camera 13 is provided in a central position between a left eye and a right eye of a wearer such that the field of view of the wearer and an imaging range of the camera 13 match each other in a case where the HMD 1 is worn. Accordingly, in a case where the surgeon D wears the HMD 1, the camera 13 images an image in the field of view of the surgeon D. Therefore, a video in a real space in which the wearer views is obtained as a background video by the camera 13. The background video is a motion picture having a predetermined frame rate.

The display 14 comprises a liquid crystal panel, and displays the background video and the superimposition image on the background video. The display 14 comprises display units for the left eye and the right eye of the wearer of the HMD 1.

The three-dimensional measurement camera 15 comprises two cameras that image the observing target tissue. The three-dimensional measurement camera 15 measures a distance between the three-dimensional measurement camera 15 and each of a plurality of points on a front surface of the observing target tissue in the real space based on two images obtained by the two cameras, and consequently measures the surface form of the observing target tissue. The distance between the three-dimensional measurement camera 15 and each of the points on the front surface of the observing target tissue is calculated by a triangulation method based on a baseline length of the two cameras of the three-dimensional measurement camera 15 and a mismatch between the two images captured by the two cameras. The three-dimensional measurement camera 15 sequentially measures the surface form of the observing target tissue in real time.

The configuration of each camera of the three-dimensional measurement camera 15 is the same as that of the aforementioned camera 13. The two cameras of the three-dimensional measurement camera 15 are arranged with the camera 13 disposed therebetween in a left-right direction, as shown in FIG. 2. The left-right direction mentioned herein is a left-right direction viewed from the wearer in a case where the wearer wears the HMD 1.

Since the three-dimensional measurement camera 15 is provided near the camera 13, it is assumed that a coordinate system of the surface form of the observing target tissue to be measured by the three-dimensional measurement camera 15 and a coordinate system of the image of the observing target tissue to be captured by the camera 13 substantially match each other. Here, in a case where these coordinate systems do not match each other, the coordinate systems may match each other by performing calibration in advance.

Although it has been described in the present embodiment that the surface form of the observing target tissue is measured by the three-dimensional measurement camera 15, the present invention is not limited thereto. The surface form of the observing target tissue may be measured by providing a distance sensor in the HMD 1.

The image display control device 4 installs an image display control program according to the embodiment of the present invention on a computer including a central processing unit (CPU) 41 and a memory 42. The image display control program is installed on the memory 42 included in the image display control device 4.

The image display control program is distributed while being recorded in a recording medium such as a digital versatile disc (DVD) and a compact disc read-only memory (CD-ROM), and is installed on the computer from the recording medium. Alternatively, the image display control program is stored while being able to access a storage device of a server computer connected to the network or a network storage, is downloaded to the computer if necessary, and is installed on the computer.

The image display control program stored in the memory 42 is executed by the CPU 41, and thus, an image extracting unit 21, a surface form obtaining unit 22, a position matching unit 23, a superimposition image generating unit 24, and a display controller 25 shown in FIG. 3 function. The configuration of the image display control device 4 may be provided in the HMD 1 in a whole or part.

A distance storage unit 26 is provided in the memory 42. The distance storage unit 26 stores information of the distance from the front surface of the observing target tissue to be used for generating the superimposition image in advance.

The image extracting unit 21 obtains the three-dimensional image V0 read out from the image storage server 3, and extracts a three-dimensional image V1 of the observing target tissue from the three-dimensional image V0. In the present embodiment, the three-dimensional image V0 obtained by imaging the abdomen of the patient is obtained from the image storage server 3, and the three-dimensional image V1 of the liver is extracted from the three-dimensional image V0. Various known image processing such as edge detection may be used as the extraction method of the three-dimensional image V1 of the liver.

Although it has been described in the present embodiment that the three-dimensional image V1 of the liver is extracted through the image processing, the present invention is not limited. For example, the three-dimensional image V0 may be displayed on the display device 6, and a liver region may be designated by a user. The designation of the liver region is accepted by a mouse included in the input device 7, and the image extracting unit 21 extracts the three-dimensional image V1 of the liver based on information of the liver region received by the input device 7.

The surface form obtaining unit 22 obtains information of the surface form of the observing target tissue measured by the three-dimensional measurement camera 15.

The position matching unit 23 performs position matching such that a positional matching relationship between the surface form of the observing target tissue obtained by the surface form obtaining unit 22 and the three-dimensional image V1 of the observing target tissue extracted by the image extracting unit 21 is established. Specifically, the position matching unit 23 according to the present embodiment generates a surface model based on the three-dimensional image V1 of the liver extracted by the image extracting unit 21. The position matching unit 23 performs the position matching by calculating the correlation between a front surface represented by the surface model and the surface form of the liver obtained by the surface form obtaining unit 22 and obtaining the positional matching relationship with which correction is the highest.

Although it has been described in the present embodiment that the position matching is performed by calculating the correlation between the surface form of the liver measured by the three-dimensional measurement camera 15 and the front surface of the three-dimensional image V1 of the liver as described above, the present invention is not limited thereto. For example, a stereoscopic image V2 generated from the surface form of the liver measured by the three-dimensional measurement camera 15 and the surface model generated based on the three-dimensional image V1 of the liver are displayed on the display device 6. The position matching may be performed in such a manner that the user may set a movement amount of the surface model by using the input device 7 while seeing a positional matching relationship between the stereoscopic image V2 and the surface model and the position matching unit 23 receives the set movement amount.

Although it has been described in the present embodiment that the position matching of the surface model of the liver is performed by using the surface form measured by the three-dimensional measurement camera 15, the present invention is not limited thereto. For example, the surface form obtaining unit 22 may obtain the image captured by the camera 13, as the information of the surface form of the liver, and the position matching unit 23 may perform the position matching such that the positional matching relationship between the image captured by the camera 13 and the surface model of the liver is established. In this case, the position matching is performed by calculating the correlation between the image captured by the camera 13 and the surface model of the liver. Various known methods may be used as the calculation model of the correlation.

The superimposition image generating unit 24 generates the superimposition image as the virtual object based on the three-dimensional image V1 of the liver on which the position matching is performed and the distance stored in advance in the distance storage unit 26. Specifically, the superimposition image generating unit 24 sets the distance from each of the points of the surface form obtained by the surface form obtaining unit 22 for the three-dimensional image V1 of the liver on which the position matching is performed, sets an opacity of 1 for the image within the distance, and sets an opacity of a value smaller than 1 for the image in a range out of the distance. That is, a transparency higher than that of the image within the distance is set for the image in the range out of the distance. The superimposition image generating unit 24 generates the superimposition image by performing volume rendering on the three-dimensional image V1 by using the opacity set in this manner.

Figure 4:
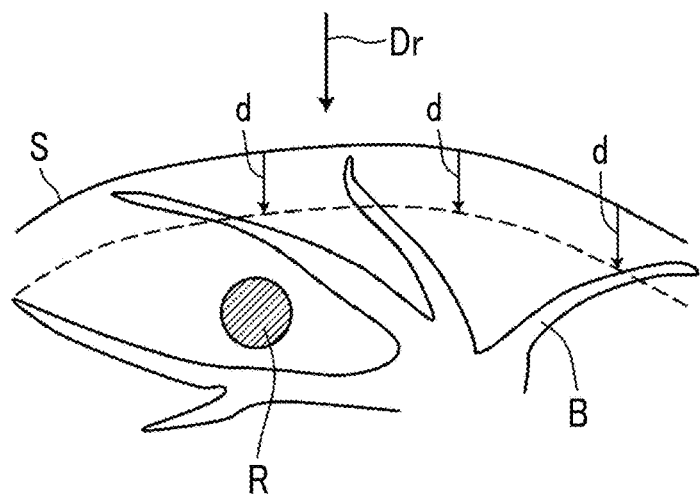
FIG. 4 is a diagram showing an example of images of portal vein and tumor included in a three-dimensional image of a liver.

FIG. 4 is a diagram showing an image B of the portal vein and image R of a tumor included in the three-dimensional image V1 of the liver. A reference S shown in FIG. 4 is a surface form obtained by the surface form obtaining unit 22, and an arrow d shown in FIG. 4 is a distance from each of points of the surface form S. An arrow Dr shown in FIG. 4 is a gaze direction of the wearer of the HMD 1. However, in the present embodiment, since the position matching of the surface form measured by the three-dimensional measurement camera 15 and the front surface of the three-dimensional image V1 is performed by providing the three-dimensional measurement camera 15 on the HMD 1, the gaze direction Dr is the same direction as the gaze direction at the time of performing the volume rendering on the three-dimensional image V1.

In a case where the distance d is set as shown in FIG. 4, the superimposition image in which the opacity of 1 is set for the image B of the portal vein included in the distance d and the opacity of the value smaller than 1 is set for the image B of the portal vein in a range out of the distance d is generated.

The opacity (transparency) to be set for the image in the range out of the distance stored in advance is optionally designated by the user by using the input device 7. The opacity (transparency) may be set such that the opacity gradually becomes lower (gradually becomes higher in the case of the transparency) as the image is farther away from the distance. The opacity is set for the image in the range out of the distance stored in advance in this manner, and thus, it is possible to display the superimposition image with which it is easier to ascertain depth information. An opacity of zero may be set such that the image in a range out of the distance is not displayed.

Since the position of the tumor is significant information in performing surgery, it is desirable that the image R of the tumor is clearly displayed. Accordingly, it is desirable that a significant tissue such as the tumor is set as a specific tissue in advance and an image of this specific tissue is clearly displayed by setting the opacity of 1 for the image of the specific tissue irrespective of the distance d similarly to the image included in the distance d.

The distance to be used at the time of generating the superimposition image may be set for each tissue to be included in the observing target tissue. For example, in a case where only the portal vein near the front surface of the liver is displayed as the superimposition image as for the portal vein included in the liver and the tumor is necessarily displayed irrespective of the distance from the front surface of the liver, the distance near the front surface of the liver may be stored in advance as for the portal vein, and a distance including a length from the front surface of the liver to a rear surface of the liver or an infinite distance may be stored in advance as for the tumor. The superimposition image for each tissue may be generated by using the distance stored for each tissue.

Although it has been described in the present embodiment that the superimposition image is generated through the volume rendering, the present invention is not limited thereto. The superimposition image may be generated by performing the surface rendering the image within the distance stored in advance.

The display controller 25 displays the superimposition image such that the superimposition image is superimposed on the background video captured by the camera 13, on the display 14 of the HMD 1. That is, the display controller 25 displays the superimposition image as the virtual object such that the superimposition image is superimposed on the liver L in the real space included in the background video. In a case where the image of the specific tissue such as the tumor is included in the superimposition image, it is desirable that the display controller 25 displays the distance of the specific tissue from the front surface of the observing target tissue as text. For example, the distance from the front surface of the observing target tissue may be calculated based on the three-dimensional image V1 of the liver.

Figure 5:
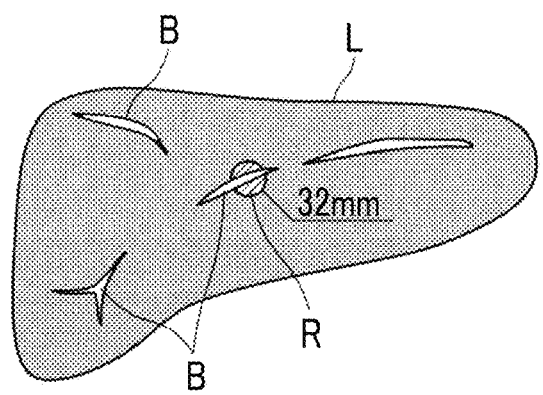
FIG. 5 is a diagram showing an example of a liver in a real space displayed on the head-mounted display and a superimposition image displayed so as to be superimposed on the liver.

FIG. 5 is a diagram showing an example of the liver L in the real space displayed on the display 14 of the HMD 1 and the superimposition image displayed so as to be superimposed on the liver L. The superimposition image shown in FIG. 5 shows a case where the opacity of 1 is set for the image B of the portal vein included in the distance stored in advance and the image R of the tumor and another image is not displayed. FIG. 5 shows an example in which a distance (32 mm) from the front surface of the liver is displayed for the image R of the tumor in a range out of the distance stored in advance.

The display controller 25 displays the superimposition image on the display unit for the left eye and the display unit for the right eye of the display 14 so as to have a parallax. Accordingly, the surgeon D can stereoscopically view the superimposition image as the virtual object.

Figure 6:
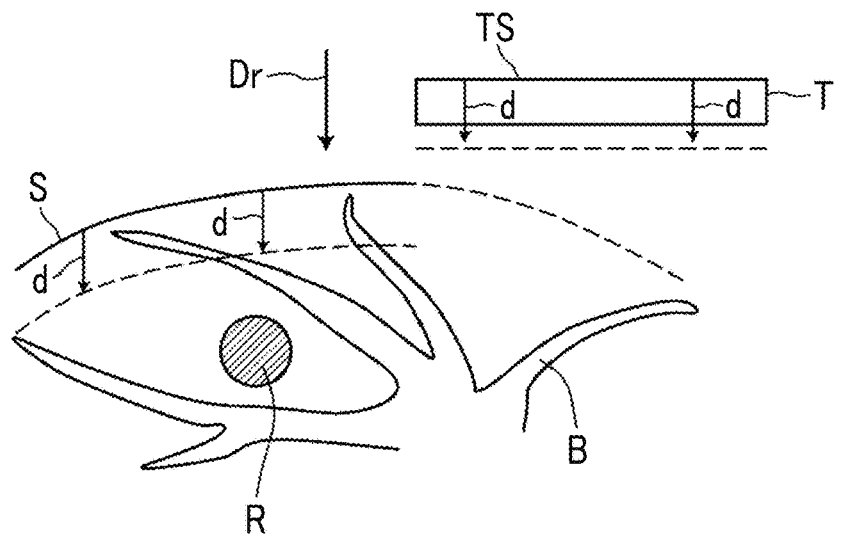
FIG. 6 is a diagram for describing actions in a case where a surgical tool is inserted between the head-mounted display and the liver in the real space.
Figure 7:
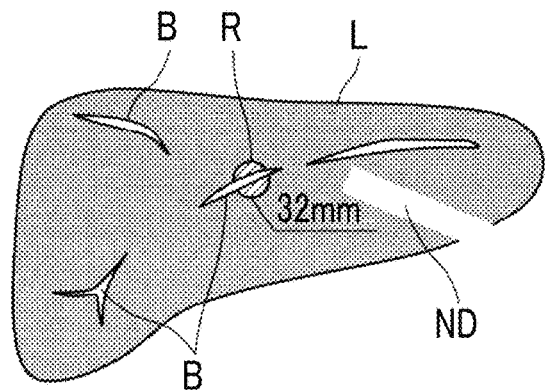
FIG. 7 is a diagram showing an example of a superimposition image in a case where the surgical tool is inserted between the head-mounted display and the liver in the real space.

FIG. 6 is a diagram for describing actions in a case where a gaze direction of the wearer toward the liver is the gaze direction Dr shown in FIG. 4 and a surgical tool T is inserted between the HMD 1 and the liver in the real space. In a case where the surgical tool T is inserted between the HMD 1 and the liver in the real space as shown in FIG. 6, the front surface measured by the three-dimensional measurement camera 15 is distinguished between a solid-line part shown in FIG. 6 on the front surface S of the liver and a front surface TS of the surgical tool T. Accordingly, the superimposition image generating unit 24 generates the superimposition image by performing the volume rendering on the image B of the portal vein from the front surface S represented by the solid line to the distance d and the image from the front surface TS of the surgical tool T to the distance d. However, there is no image in the range from the front surface TS of the surgical tool T to the distance d in reality. Therefore, the superimposition image in which the range of the surgical tool T is a blank image ND as shown in FIG. 7 is generated and displayed so as to be superimposed, as the superimposition image. JP2012-235983A suggests that the superimposition image is restrained from being displayed so as to be superimposed on the surgical tool by detecting the position of the surgical tool. However, according to the present embodiment, it is possible to restrain the superimposition image from being displayed so as to be superimposed on the surgical tool without providing a sensor that detects the surgical tool, and thus, it is possible to display the superimposition image which it is easier to be seen.

Figure 8:
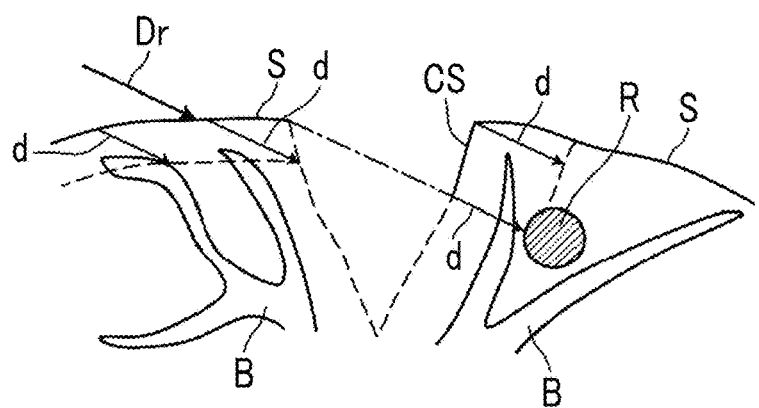
FIG. 8 is a diagram for describing the generation of a superimposition image in a case where a part of the liver is resected during surgery.
Figure 9:
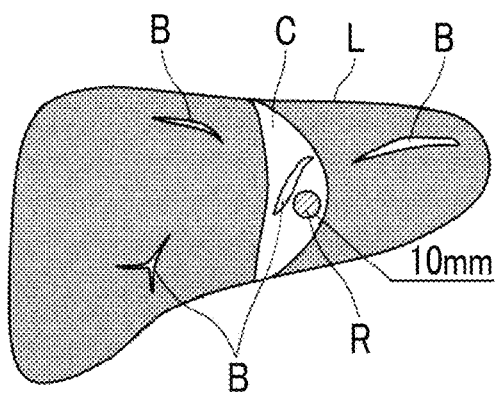
FIG. 9 is a diagram showing an example of the superimposition image in a case where a part of the liver is resected during the surgery.

For example, even in a case where a part of the liver L is resected during the surgery and the gaze direction of the wearer of the HMD 1 is the gaze direction Dr shown in FIG. 8, a superimposition image obtained by performing the volume rendering on an image within the distance d from a resection surface CS and the front surface S of the liver L represented by the solid line in FIG. 8 is generated and displayed so as to be superimposed. Accordingly, even though the three-dimensional image in which a part of the three-dimensional image V1 of the liver is resected is not generated, it is possible to display the superimposition image including the image B of the portal vein near the resection surface or the image R of the tumor as shown in FIG. 9. Therefore, it is possible to reduce a load in arithmetic processing.

In a case where a part of the liver L is resected during the surgery and the surface form of the liver L is deformed by being pressed, the superimposition image may be generated by using the deformed three-dimensional image V1 by performing deforming corresponding to the deformation of the liver on the three-dimensional image V1 of the liver to be used at the time of generating the superimposition image.

Figure 10:
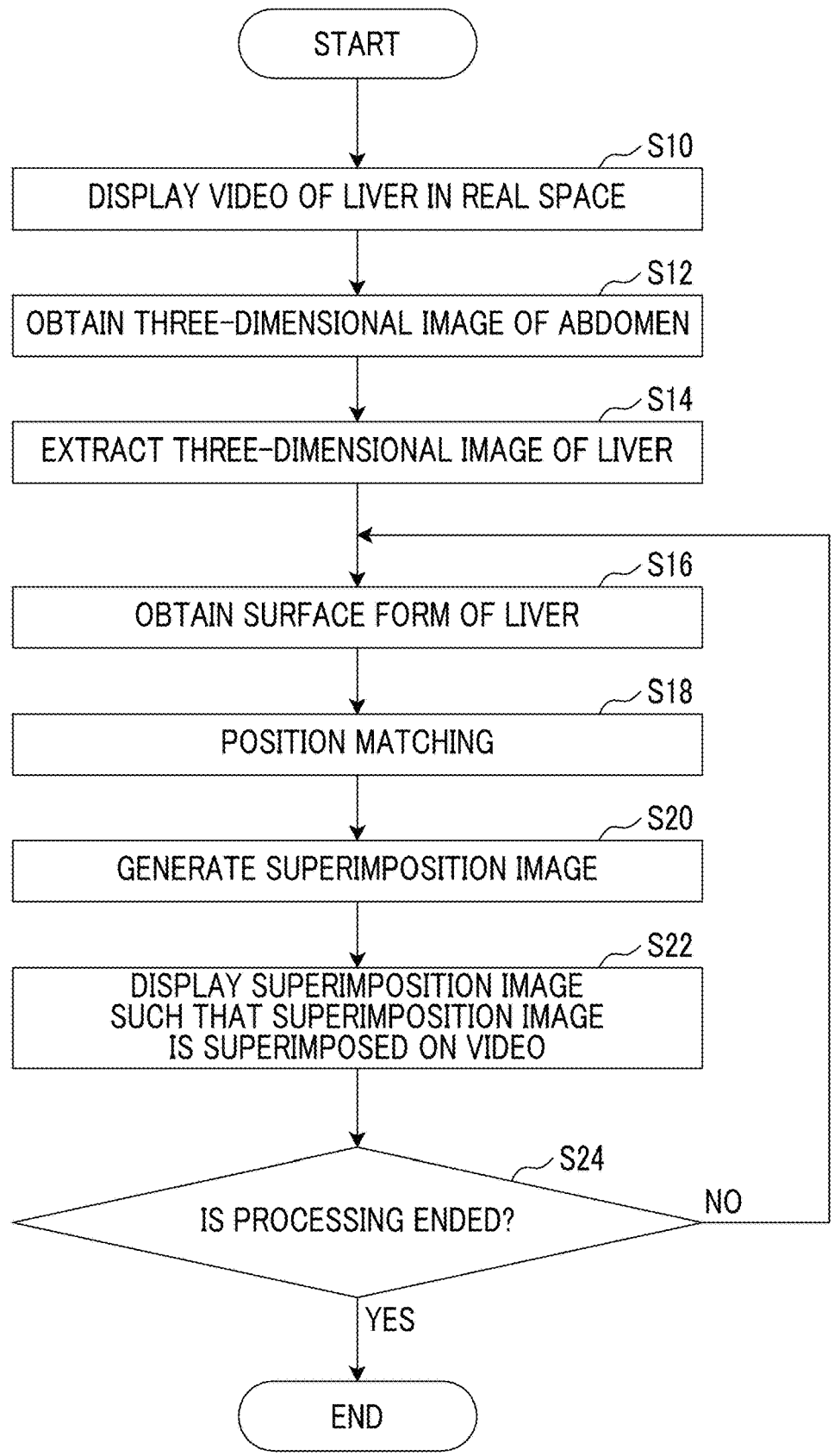
FIG. 10 is a flowchart for describing actions of the virtual object display system using the embodiment of the image display control device according to the present invention.

Next, an action of the virtual object display system according to the present embodiment will be described with reference to a flowchart shown in FIG. 10. Hereinafter, a case where the observing target tissue is the liver will be described.

Initially, the liver in the real space is captured by the camera 13 of the HMD 1, and the video of the liver is displayed as the background video on the display 14 (S10).

The three-dimensional image V0 of the abdomen captured in advance is obtained by the image extracting unit 21 (S12), and the image extracting unit 21 extracts the three-dimensional image V1 of the liver from the three-dimensional image V0 (S14).

Subsequently, the surface form of the liver is measured by the three-dimensional measurement camera 15 of the HMD 1, and the information of the surface form is obtained by the surface form obtaining unit 22 (S16).

The surface form obtained by the surface form obtaining unit 22 is input to the position matching unit 23, and the position matching unit 23 performs the position matching such that the positional matching relationship between the input surface form and the front surface of the three-dimensional image V1 of the liver is established (S18).

The distance stored in the distance storage unit 26 in advance is read out by the superimposition image generating unit 24, and the superimposition image generating unit 24 generates the superimposition image as the virtual object based on the readout distance and the three-dimensional image V1 of the liver on which the position matching is performed (S20).

The superimposition image generated by the superimposition image generating unit 20 is input to the display controller 25, and the display controller 25 outputs a display control signal to the HMD 1 such that the superimposition image is displayed on the display 14 of the HMD 1. The display control signal output from the display controller 25 is received by the HMD 1, and the display 14 of the HMD 1 displays the superimposition image such that the superimposition image is superimposed on the video of the liver captured by the camera 13 (S22).

The processing from S16 to S22 is repeatedly performed until an instruction to end the displaying of the superimposition image is input by the wearer of the HMD 1 (S24, NO). That is, the surface form of the liver in the real space is obtained by the surface form obtaining unit 22 by sequentially performing the measurement using the three-dimensional measurement camera 15, and the position matching is sequentially performed by the position matching unit 23 according to the obtaining of the surface form thereof. The superimposition image is sequentially updated according to the position matching, and the superimposition image is displayed so as to be superimposed on the video of the liver on the display 14 of the HMD 1.

In a case where the instruction to end the displaying of the superimposition image is input by the wearer of the HMD 1, the displaying of the superimposition image is ended (S24, YES).

According to the virtual object display system according to the aforementioned embodiment, the three-dimensional image V1 of the observing target tissue is extracted from the three-dimensional image V0 obtained by imaging the testing subject, the surface form of the observing target tissue in the real space is obtained, and the position matching is performed such that the positional matching relationship between the surface form in the real space and the three-dimensional image V1 of the observing target tissue is established. The superimposition image is generated based on the three-dimensional image V1 of the observing target tissue on which the position matching is performed and the distance stored in advance, and the superimposition image is displayed so as to be superimposed on the observing target tissue. The superimposition image with which it is easy to ascertain the depth information can be displayed so as to be superimposed on the observing target tissue in the real space by generating the superimposition image corresponding to the distance stored in advance in this manner and displaying the superimposition image such that the superimposition image is superimposed on the observing target tissue.

Although it has been described in the aforementioned embodiment that the distance to be used for generating the superimposition image is stored in the distance storage unit 26 in advance, the distance may be changed. The change of the distance may be accepted by the input device 7. In this case, the input device 7 corresponds to a distance change accepting unit according to the embodiment of the present invention. The superimposition image generating unit 24 generates the superimposition image based on the changed distance similarly to the aforementioned embodiment. As stated above, the distance can be changed, and thus, it is possible to generate various superimposition images corresponding to requests of the wearer.

Although it has been described in the aforementioned embodiment that the camera 13 is provided on the HMD 1, the camera 13 may be provided as a member separately from the HMD 1. In this case, it is preferable that the camera is disposed so as to image a range corresponding to the field of view of the wearer of the HMD 1.

Although it has been described in the aforementioned embodiment that a so-called projection type HMD 1 that displays the background video in the real space captured by the camera 13 on the display 14 of the HMD 1 is used, the HMD 1 is not limited thereto. The display controller 25 may display only the superimposition image on a see-through type display by using the HMD including the see-through type display. In this case, the wearer of the HMD 1 can observe an image on which a virtual image of the superimposition image is displayed so as to be superimposed on the observing target tissue such as the liver in the real space.

Although it has been described in the aforementioned embodiment that the superimposition image is displayed on the HMD 1, the background video captured by the camera and the superimposition image may be displayed on a display of a tablet terminal having the camera and the three-dimensional measurement camera mounted thereon, instead of the HMD 1.

Although it has been described in the aforementioned embodiment that the observing target tissue is the liver, the present invention is not limited to the liver. For example, in a case where surgery is performed on an organ such as heart, lungs, or colon, a superimposition image thereof may be generated, and the generated superimposition image may be displayed so as to be superimposed on the organ in the real space. The present invention is not limited to the medial image. For example, a superimposition image may be generated based on a three-dimensional image such as an industrial product, and the superimposition image may be displayed so as to be superimposed on an industrial product in the real space.

EXPLANATION OF REFERENCES

1: head-mounted display
2: three-dimensional image imaging device
3: image storage server
4: image display control device
5: network
6: display device
7: input device
11: CPU
12: memory
13: camera
14: display
15: three-dimensional measurement camera
20: superimposition image generating unit
21: image extracting unit
22: surface form obtaining unit
23: position matching unit
24: superimposition image generating unit
25: display controller
26: distance storage unit
41: CPU
42: memory
CS: resection surface
d: distance from front surface of observing target tissue
D: surgeon
Dr: gaze direction
L: liver
ND: blink image
R: image of tumor
B: image of portal vein
S: surface form
T: surgical tool
TS: front surface of surgical tool

What is claimed is:
1. An image display control device comprising:
a processor configured to
extract an image of an observing target tissue from a three-dimensional image obtained by imaging a testing subject;
a distance storage that stores a distance from a front surface of the observing target tissue to be used for generating a superimposition image to be displayed so as to be superimposed on the observing target tissue;
obtain a surface form of the observing target tissue in a real space;
perform position matching such that a positional matching relationship between the surface form in the real space and the image of the observing target tissue is established;

generate the superimposition image based on the image of the observing target tissue on which the position matching is performed and the distance stored in the distance storage; and display the superimposition image such that the superimposition image is superimposed on the observing target tissue, wherein the processor generates the superimposition image by setting a transparency higher than a transparency of the image of the observing target tissue within the distance for the image of the observing target tissue in a range out of the distance.

2. The image display control device according to claim 1, wherein the processor obtains the surface form measured by a three-dimensional measurement camera that measures the surface form of the observing target tissue in the real space, and the processor measures the surface form by measuring a distance between the three-dimensional measurement camera and each of a plurality of points on the front surface of the observing target tissue in the real space.

3. The image display control device according to claim 2, wherein the processor sequentially obtains the surface form in the real space with elapse of time, the processor sequentially performs the position matching according to the obtaining of the surface form, and the processor sequentially updates the superimposition image according to the position matching.

4. The image display control device according to claim 2, the processor further configured to:

accept a change of the distance, wherein the processor generates the superimposition image based on the changed distance and the image of the observing target tissue.

5. The image display control device according to claim 2, further comprising:

a camera that images the image of the observing target tissue in the real space, wherein the processor displays the superimposition image such that the superimposition image is superimposed on the image of the observing target tissue captured by the camera.

6. The image display control device according to claim 2, wherein the processor displays the superimposition image on a see-through type monitor.

7. The image display control device according to claim 1, wherein the processor sequentially obtains the surface form in the real space with elapse of time, the processor sequentially performs the position matching according to the obtaining of the surface form, and the processor sequentially updates the superimposition image according to the position matching.

8. The image display control device according to claim 7, the processor further configured to:

accept a change of the distance, wherein the processor generates the superimposition image based on the changed distance and the image of the observing target tissue.

9. The image display control device according to claim 7, further comprising:

a camera that images the image of the observing target tissue in the real space, wherein the processor displays the superimposition image such that the superimposition image is superimposed on the image of the observing target tissue captured by the camera.

10. The image display control device according to claim 1, the processor further configured to:

accept a change of the distance, wherein the processor generates the superimposition image based on the changed distance and the image of the observing target tissue.

11. The image display control device according to claim 1, wherein the transparency set for the image of the observing target tissue in the range out of the distance is set so as to gradually become higher as the image is farther away from the distance.

12. The image display control device according to claim 1, wherein the processor generates the superimposition image by setting the same opacity as an opacity of the image of the observing target tissue within the distance for an image of a preset specific tissue in the range out of the distance.

13. The image display control device according to claim 12, wherein, in a case where the image of the specific tissue is displayed, the processor displays, as text, a distance of the specific tissue from the front surface of the observing target tissue.

14. The image display control device according to claim 1, further comprising:

a camera that images the image of the observing target tissue in the real space, wherein the processor displays the superimposition image such that the superimposition image is superimposed on the image of the observing target tissue captured by the camera.

15. The image display control device according to claim 1, wherein the processor displays the superimposition image on a see-through type monitor.

16. An image display control method comprising:

extracting an image of an observing target tissue from a three-dimensional image obtained by imaging a testing subject;

storing a distance from a front surface of the observing target tissue to be used for generating a superimposition image to be displayed so as to be superimposed on the observing target tissue in advance;

obtaining a surface form of the observing target tissue in a real space;

performing position matching such that a positional matching relationship between the surface form in the real space and the image of the observing target tissue is established;

generating the superimposition image based on the image of the observing target tissue on which the position matching is performed and the distance stored in advance; and displaying the superimposition image such that the superimposition image is superimposed on the observing target tissue, wherein generating the superimposition image includes setting a transparency higher than a transparency of the image of the observing target tissue within the distance for the image of the observing target tissue in a range out of the distance.

17. A non-transitory computer readable recording medium storing an image display control program causing a computer to perform:

a procedure of extracting an image of an observing target tissue from a three-dimensional image obtained by imaging a testing subject;

a procedure of storing a distance from a front surface of the observing target tissue to be used for generating a superimposition image to be displayed so as to be superimposed on the observing target tissue in advance;

a procedure of obtaining a surface form of the observing target tissue in a real space;

a procedure of performing position matching such that a positional matching relationship between the surface form in the real space and the image of the observing target tissue is established;

a procedure of generating the superimposition image based on the image of the observing target tissue on which the position matching is performed and the distance stored in advance; and a procedure of displaying the superimposition image such that the superimposition image is superimposed on the observing target tissue, wherein generating the superimposition image includes setting a transparency higher than a transparency of the image of the observing target tissue within the distance for the image of the observing target tissue in a range out of the distance.

* * * * *